US012678106B2

(12) United States Patent
Lu et al.

(10) Patent No.: US 12,678,106 B2
(45) Date of Patent: Jul. 14, 2026

(54) FATIGUE ESTIMATION DEVICE, FATIGUE ESTIMATION METHOD, AND STORAGE MEDIUM

(71) Applicant: NEC Corporation, Tokyo (JP)

(72) Inventors: Jingwen Lu, Tokyo (JP); Tasuku Kitade, Tokyo (JP); Masanori Tsujikawa, Tokyo (JP)

(73) Assignee: NEC CORPORATION, Tokyo (JP)

( * ) Notice: Subject to any disclaimer, the term of this patent is extended or adjusted under 35 U.S.C. 154(b) by 281 days.

(21) Appl. No.: 18/564,761

(22) PCT Filed: Jun. 1, 2021

(86) PCT No.: PCT/JP2021/020836
§ 371 (c)(1),
(2) Date: Nov. 28, 2023

(87) PCT Pub. No.: WO2022/254574
PCT Pub. Date: Dec. 8, 2022

(65) Prior Publication Data
US 2024/0268769 A1      Aug. 15, 2024

(51) Int. Cl.
*A61B 5/00*          (2006.01)
(52) U.S. Cl.
CPC .................................. *A61B 5/7275* (2013.01)
(58) Field of Classification Search
CPC ..................................................... A61B 5/7275
See application file for complete search history.

(56) References Cited

U.S. PATENT DOCUMENTS 8,512,240 B1 * 8/2013 Zuckerman-Stark ........................
A61B 5/0261
128/924
2017/0127992 A1    5/2017   Takahashi
2019/0167173 A1    6/2019   Fujii et al.
2019/0343459 A1   11/2019   Korzinov et al.

FOREIGN PATENT DOCUMENTS

CN      110448281   A    11/2019
JP      2017-023311  A    2/2017
JP      2017-086524  A    5/2017
JP      107590358   A    1/2018
JP      2018-023676  A    2/2018

OTHER PUBLICATIONS

International Search Report for PCT Application No. PCT/JP2021/020836, mailed on Aug. 24, 2021.

* cited by examiner

*Primary Examiner* — Alyssa M Alter

(57) ABSTRACT

In a fatigue estimation device mainly includes a normalization process means 14X, and a fatigue estimation means 16X. The normalization process means 14X performs a normalization process based on an attribute of a test subject with respect to biological data of the test subject. The fatigue estimation means 16X estimates a fatigue level of the test subject based on the biological data after the normalization process.

9 Claims, 7 Drawing Sheets

<u>100</u>: FATIGUE ESTIMATION SYSTEM

1

100A

START

S21

PERFORM NORMALIZATION PROCESS
BASED ON ATTRIBUTE OF TEST SUBJECT
WITH RESPECT TO BIOLOGICAL DATA
OF TEST SUBJECT

S22

ESTIMATE FATIGUE LEVEL OF TEST
SUBJECT BASED ON BIOLOGICAL DATA
AFTER NORMALIZATION PROCESS

END

FATIGUE ESTIMATION DEVICE, FATIGUE ESTIMATION METHOD, AND STORAGE MEDIUM

This application is a National Stage Entry of PCT/JP2021/020836 filed on Jun. 1, 2021, the contents of all of which are incorporated herein by reference, in their entirety.

TECHNICAL FIELD

The present disclosure relates to a fatigue estimation device, a fatigue estimation method, and a storage medium for estimating fatigue.

BACKGROUND ART

A device or system for estimating a fatigue level of a test subject is known. For example, Patent Document 1 discloses a fatigue level management system in which biological data including a pulse rate of a user are calculated based on a pulse wave signal output from a pulse wave detection means and the fatigue level is determined based on the calculated biological data.

PRECEDING TECHNICAL REFERENCES

Patent Document

Patent Document 1: Japanese Laid-open Patent Publication No. 2017-086524

SUMMARY

Problem to be Solved by the Invention

There are individual differences in a fatigue level according to a test subject, and such individual differences cannot be considered only by biological data used for fatigue estimation. Therefore, it is necessary to carry out a fatigue estimation considering such individual differences.

It is one object of the present disclosure to provide a fatigue estimation device, a fatigue estimation method, and a storage medium capable of suitably estimating fatigue in view of the problem described above.

Means for Solving the Problem

According to an example aspect of the present disclosure, there is provided a fatigue estimation device including:
  a normalization process means configured to perform a normalization process based on an attribute of a test subject with respect to biological data of the test subject; and
  a fatigue estimation means configured to estimate a fatigue level of the test subject based on the biological data after the normalization process.

According to another example aspect of the present disclosure, there is provided a fatigue estimation method performed by a computer, the fatigue estimation method including:
  performing a normalization process based on an attribute of a test subject with respect to biological data of the test subject; and
  estimating a fatigue level of the test subject based on the biological data after the normalization process. Note that a "computer" may include any electronic device (even a processor in an electronic device) and may be formed by a plurality of electronic devices.

According to a further example aspect of the present disclosure, there is provided a recording medium storing a program, the program causing a computer to perform a process including:
  performing a normalization process based on an attribute of a test subject with respect to biological data of the test subject; and
  estimating a fatigue level of the test subject based on the biological data after the normalization process.

Effect of the Invention

According to the present disclosure, it becomes possible to accurately estimate a fatigue level of a test subject.

EXAMPLE EMBODIMENTS

In the following, example embodiments of a fatigue estimation device, a fatigue estimation method, and a storage medium will be described with reference to the drawings.

First Example Embodiment

(1) System Configuration

Figure 1:
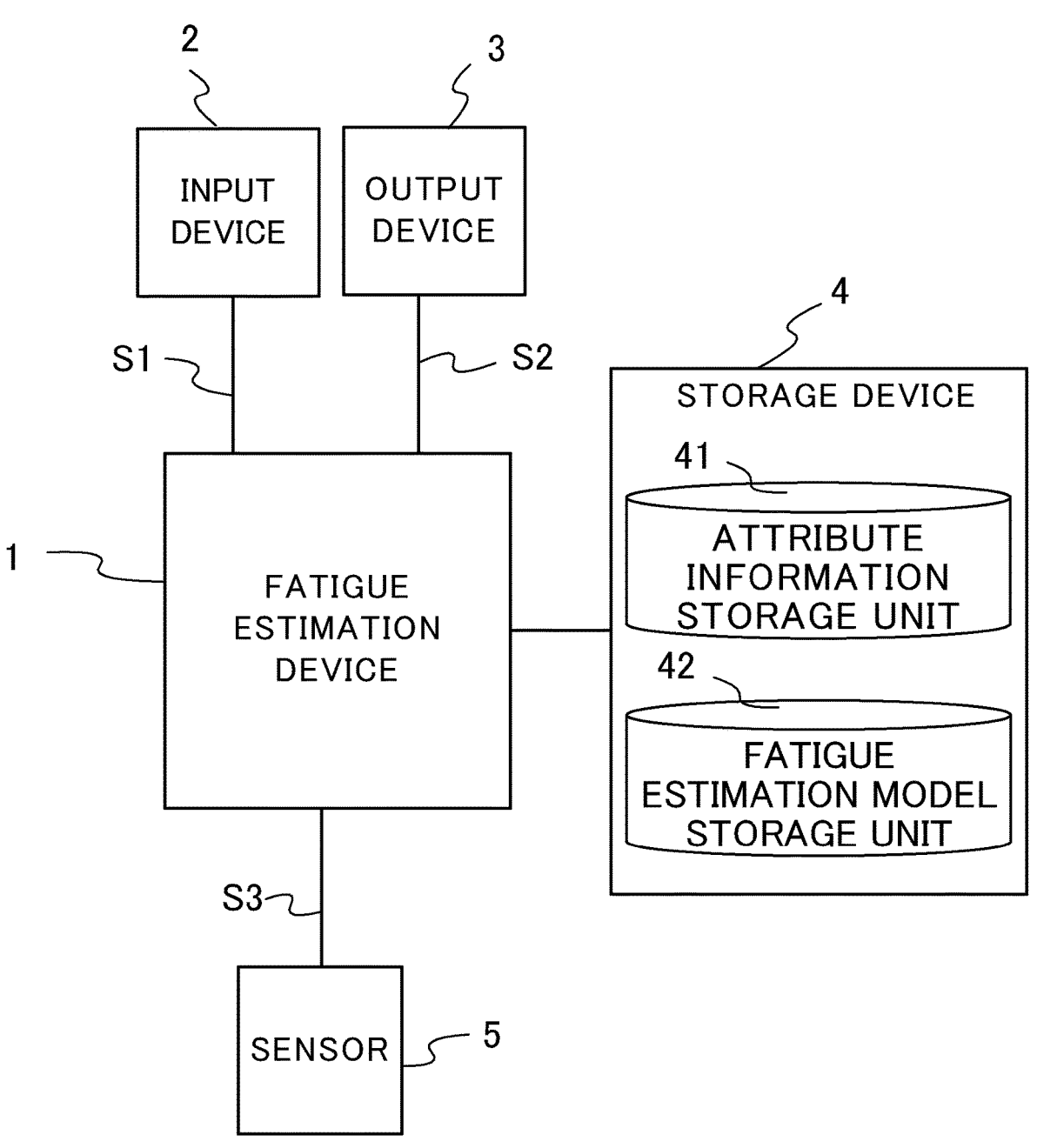
FIG. 1 illustrates a schematic configuration of a fatigue estimation system according to a first example embodiment.

FIG. 1 illustrates a schematic configuration of a fatigue estimation system 100 according to a first example embodiment. The fatigue estimation system 100 performs processing related to estimation of fatigue of a test subject. The fatigue estimation system 100 mainly includes a fatigue estimation device 1, an input device 2, an output device 3, a storage device 4, and a sensor 5.

The fatigue estimation device 1 performs data communications with the input device 2, the output device 3, and the sensor 5 through a communication network or through a direct communication by a wireless or wire channel. Then, the fatigue estimation device 1 determines a fatigue state of the test subject based on an input signal "S1" supplied from the input device 2, a sensor signal "S3" supplied from the sensor 5, and information stored in the storage device 4. Moreover, the fatigue estimation device 1 generates an output signal "S2" based on the fatigue determination result of the test subject, and supplies the output signal S2 generated to the output device 3.

The input device 2 is an interface for receiving a manual input (external input) of information concerning each test subject. Note that the user who inputs information using the input device 2 may be the test subject himself/herself or may be a person who manages or supervises activities of the test subject. The input device 2 may be various user input interfaces such as a touch panel, a button, a keyboard, a mouse, and a voice input device, for instance. The input device 2 supplies the generated input signal S1 to the fatigue estimation device 1. The output device 3 displays predetermined information or outputs sounds based on the output signal S2 supplied from the fatigue estimation device 1. The output device 3 is a display, a projector, a speaker, or the like, for example.

The sensor 5 measures biological signals or the like of the test subject, and supplies the measured biological signal or the like to the fatigue estimation device 1 as a sensor signal S3. In this case, the sensor signal S3 may be any biological data (including vital information) such as a heart rate, an EEG, perspiration, hormone secretion, a cerebral blood flow, a blood pressure, a body temperature, an electromyography, an electrocardiography, and a respiration rate. The sensor 5 may be a device which analyzes blood collected from the test subject and outputs the sensor signal S3 indicating an analysis result. The sensor 5 may be a device which performs a physical measurement such as jumping to measure physical fatigue or the like.

The storage device 4 is a memory which stores various types of information necessary for a calculation of various fatigue levels. The storage device 4 may be an external storage device such as a hard disk which is connected to or built into the fatigue estimation device 1, or may be a storage medium such as a flash memory. The storage device 4 may be a server device which performs data communication with the fatigue estimation device 1. Moreover, the storage device 4 may be formed by a plurality of devices.

The storage device 4 functionally includes an attribute information storage unit 41 and a fatigue estimation model storage unit 42.

The attribute information storage unit 41 stores attribute information concerning an attribute for each the test subject. The attribute information is, for instance, a muscle mass (that is, a weight of muscle tissues) or information related to the muscle mass (that is, information related to a type of sport the test subject performs or a position of the test subject in a case where the test subject is an athlete) for each test subject. Note that the muscle mass can be measured by a body composition analyzer using, for instance, a bio-impedance method or a DXA (Dual Energy X-ray Absorptiometry method or the like.

Incidentally, the attribute information stored in the attribute information storage unit 41 is not limited to information concerning the muscle mass, but may be information indicating another attribute of the test subject such as an age, a gender, an occupation, a present illness and past medical history, a type of sport or position in the sport in a case where the test subject is an athlete, or a position in that sport. Moreover, in a case where the attribute information is stored for each of a plurality of persons in the attribute information storage unit 41, the attribute information is stored in the attribute information storage unit 41 in association with identification information of a corresponding person.

Preferably, the attribute information stored in the attribute information storage unit 41 may be periodically updated depending on a state of the test subject. For instance, the attribute information stored in the attribute information storage unit 41 may determine an update frequency depending on a type of the attribute or an activity status of the test subject. For instance, in a case where information of the muscle mass of the athlete is stored as attribute information in the attribute information storage unit 41, the update frequency of the attribute information may be different depending on whether or not the athlete is in season. Note that the update of the attribute information stored in the attribute information storage unit 41 may be performed by the fatigue estimation device 1 or may be performed by a device other than the fatigue estimation device 1.

The fatigue estimation model storage unit 42 stores information concerning a fatigue estimation model which is a model for calculating the fatigue level based on features of the biological data of the test subject. For instance, when the fatigue estimation model is a linear model, the fatigue estimation model storage unit 42 stores information of parameters (weights) of the linear model. The fatigue estimation model is not limited to the linear model, and may be a regression model (statistical model) or a machine learning model other than the linear model. In these cases, the fatigue estimation model storage unit 42 stores information of parameters necessary for configuring the fatigue estimation model. For instance, when the fatigue estimation model is a model based on a neural network such as a convolution neural network, the fatigue estimation model storage unit 42 stores information of various parameters such as the layer structure, a neuron structure of each layer, a number of filters and a filter size in each layer, and the weight of each element of each filter.

Note that the configuration of the fatigue estimation system 100 illustrated in FIG. 1 is an example, various changes may be made to the configuration. For instance, the input device 2 and the output device 3 may be configured integrally. In this case, the input device 2 and the output device 3 may be formed as tablet type terminal which is integrated into or is separated from the fatigue estimation device 1. Moreover, the input device 2 and the sensor 5 may be formed integrally. Alternately, the fatigue estimation device 1 may be composed of a plurality of devices. In this case, a plurality of devices forming the fatigue estimation device 1 exchange information necessary to execute processes allocated in advance between these devices.

(2) Hardware Configuration of Fatigue Estimation Device

Figure 2:
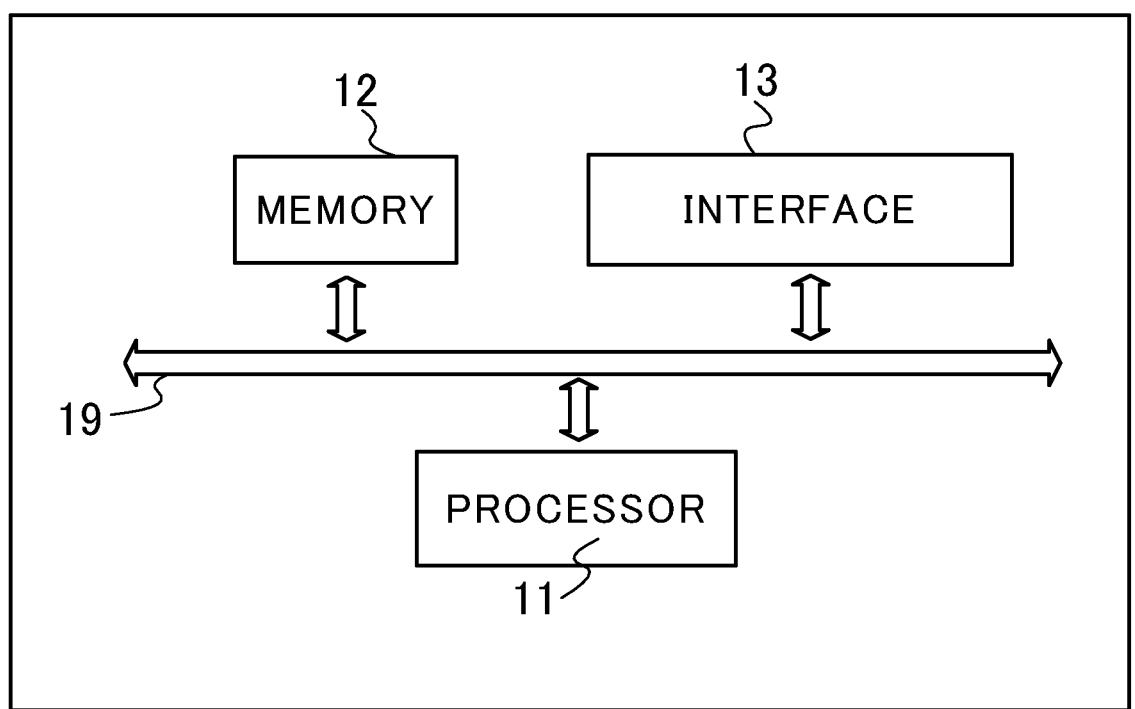
FIG. 2 illustrates a hardware configuration of a fatigue estimation device.

FIG. 2 illustrates the hardware configuration of the fatigue estimation device 1. The fatigue estimation device 1 includes a processor 11, a memory 12, and an interface 13 as hardware. The processor 11, the memory 12 and the interface 13 are connected via a data bus 19.

The processor 11 functions as a controller (arithmetic unit) for performing an overall control of the fatigue estimation device 1 by executing programs stored in the memory 6. The processor 11 may be, for instance, a CPU (Central Processing Unit), a GPU (Graphics Processing Unit), a TPU (Tensor Processing Unit), or the like. The processor 11 may be formed by a plurality of processors. The processor 11 corresponds to an example of a computer.

The memory 12 may be formed by a variety of volatile and non-volatile memories such as a RAM (Random Access Memory), a ROM (Read Only Memory, and a flash memory. Moreover, in the memory 12, programs for executing processes of the fatigue estimation device 1 executes are stored. Note that, a part of the information stored in the memory 12 may be stored by one or a plurality of external storage devices capable of communicating with the fatigue estimation device 1, or may be stored by a removable storage medium with respect to the fatigue estimation device 1.

The interface 13 is an interface for electrically connecting the fatigue estimation device 1 and other devices. These interfaces may be wireless interfaces such as network adapters, for sending and receiving data to and from other devices wirelessly, or may be hardware interfaces for connecting devices such as cables to other devices.

Note that the hardware configuration of the fatigue estimation device 1 is not limited to the configuration illustrated in FIG. 2. For instance, the fatigue estimation device 1 may include at least one of the input device 2 or the output device 3. Moreover, the fatigue estimation device 1 may be connected or built into the sound output device such as a speaker.

(3) Functional Block

Figure 3:
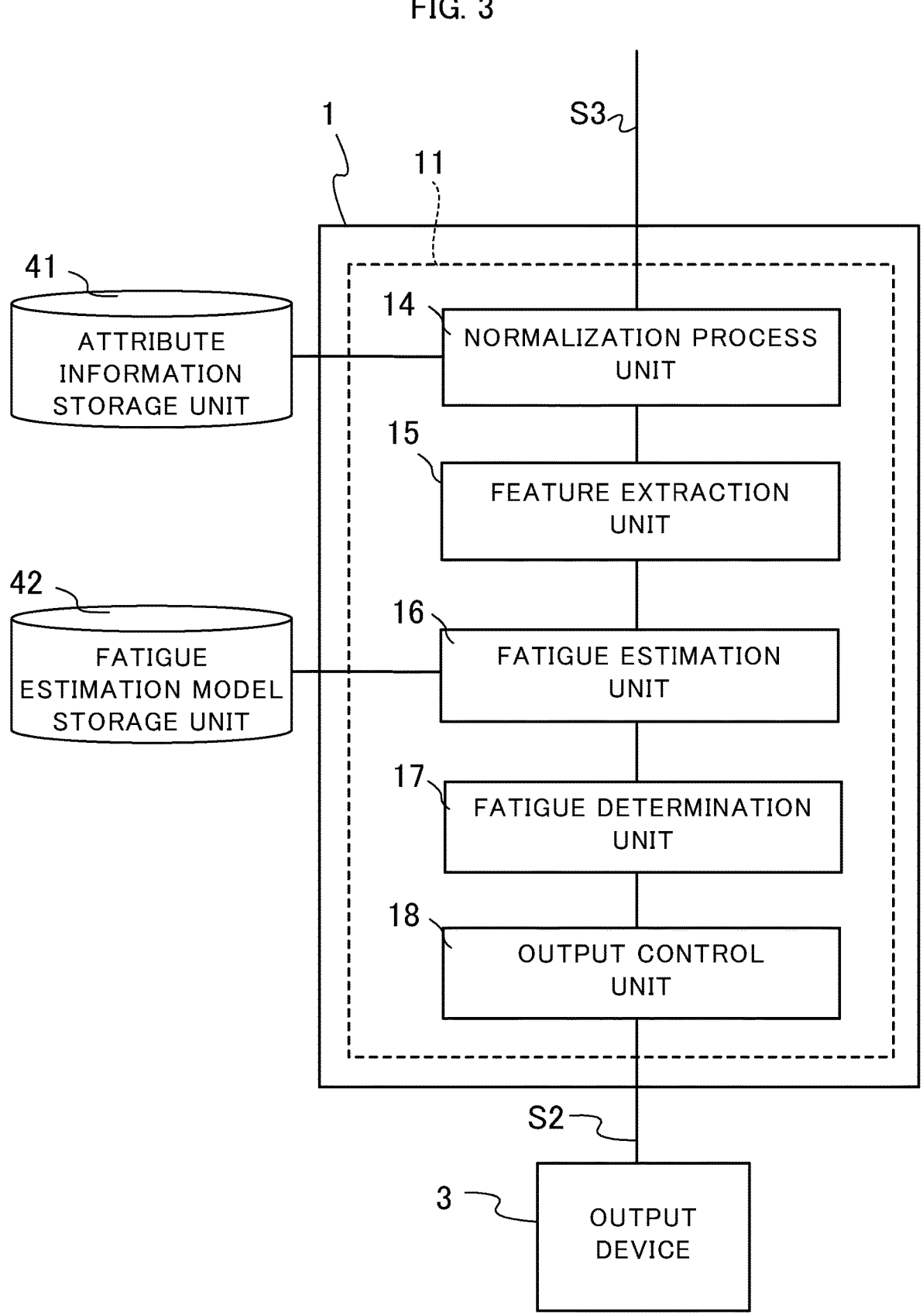
FIG. 3 illustrates an example of functional blocks of the fatigue estimation device.

FIG. 3 is an example of a functional block of the fatigue estimation device 1. The processor 11 of the fatigue estimation device 1 functionally includes a normalization process unit 14, a feature extraction unit 15, a fatigue estimation unit 16, a fatigue determination unit 17, and an output control unit 18. Not that in FIG. 3, blocks for sending and receiving data are connected by solid lines, but the combination of blocks for sending and receiving data is not limited to FIG. 3. The same applies to the drawings of other functional blocks described below.

The normalization process unit 14 performs a normalization process for adjust differences based on respective attributes of test subjects with respect to biomedical data represented by the sensor signal S3, based on the attribute information of the test subject stored in the attribute information storage unit 41. In this instance, the normalization process unit 14 inputs the biological data of the test subject represented by the sensor signal S3 and the attribute information of the test subject, and outputs the normalized biological data (also referred to as "normalized biological data Dn") to adjust differences based on the attributes of the test subjects. The normalization process unit 14 may perform the normalization process using any normalization technique such as a max-min normalization, a z-score normalization, or the like. Note that in a case of acquiring the attribute information of the test subject from the attribute information storage unit 41, the normalization process unit 14 acquires the identification information of the test subject by, for instance, login information of the test subject or arbitrary person recognition process (for instance, a biometric authentication using a camera image or the like), and acquires the attribute information associated with the identification information from the attribute information storage unit 41.

For instance, in a case of estimating the physical fatigue, the normalization process unit 14 normalizes a heart rate interval (RRI:R-R Interval) of the test subject represented by the sensor signal S3 based on the muscle mass of the test subject stored in the attribute information storage unit 41.

The feature extraction unit 15 performs a process for extracting features for the normalized biological data Dn output from the normalization process unit 14, and outputs the extracted features of the normalized biological data Dn to the fatigue estimation unit 16. In this case, the feature extraction unit 15 may perform a process for extracting various features used for a fatigue estimation. For instance, parameters of the feature extraction model may be stored in the storage device 4 or the memory 12. In this case, the feature extraction unit 15 acquires features of the normalized biological data Dn by forming a feature extraction model based on the parameters which have been stored and inputting the normalized biological data Dn to the feature extraction model.

For instance, in a case where the biological data represented by the sensor signal S3 is time series data of the heart rate interval (RRI), the feature extraction unit 15 calculates the heart rate variability which is an index of an autonomic neural tension as the features. The heart rate variability is, for instance, a representative value of the RRI (a mean, a maximum, a minimum, an average, or the like) and/or an indicator value of a RRI variability (a standard deviation, a variance, or the like).

The fatigue estimation unit 16 calculates a fatigue level of the test subject (also referred to as a "test subject fatigue level Df") using the fatigue estimation model stored in the fatigue estimation model storage unit 42 based on the features of the normalized biological data Dn supplied from the feature extraction unit 15. Specifically, the fatigue estimation unit 16 acquires the fatigue level of the test subject output by the fatigue estimation model by inputting the features of the normalized biological data Dn into the fatigue estimation model as the test subject fatigue level Df. Note that the test subject fatigue level Df may be a physical fatigue level, a mental fatigue level, an overall fatigue level totaling all of these levels, and a combination thereof. For instance, the fatigue estimation unit 16 calculates a physical fatigue score of the test subject as the test subject fatigue level Df by inputting the features of the normalized biological data Dn, which represents a jump height of the test subject, into the fatigue estimation model.

The fatigue determination unit 17 performs a determination relating to fatigue of the test subject based the test subject fatigue level Df which the fatigue estimation unit 16 has calculated. For instance, the fatigue determination unit 17 compares the test subject fatigue level Df with a threshold value previously stored in the storage device 4 or the memory 12 to determine whether or not the test subject is in a high fatigue state for which attention or action is needed. For instance, the fatigue determination unit 17 determines that the test subject is in the high fatigue state when the fatigue estimation unit 16 calculates the calculated physical fatigue score as the test subject fatigue level Df is equal to or greater than 70 or more out of 100 points. Note that in order to classify the fatigue state in stages, a plurality of threshold values may be provided.

The output control unit 18 outputs a determination result by the fatigue determination unit 17. For instance, the output control unit 18 displays the determination result acquired by the fatigue determination unit 17 on a display unit, or outputs sound by a sound output unit. In another example, the output control unit 18, the determination result by the fatigue determination unit 17, and stores it in the storage device 4. In this case, the output control unit 18 may output information concerning the test subject fatigue level Df calculated by the fatigue estimation unit 16, together with the determination result acquired by the fatigue determination unit 17.

Incidentally, each component of the normalization process unit 14, the feature extraction unit 15, the fatigue estimation unit 16, the fatigue determination unit 17, and the output control unit 18 which are described in FIG. 3, for instance, the processor 11 can be realized by executing programs. Alternatively, the necessary programs may be recorded on any non-volatile storage medium and installed as needed to realize each component. Note that at least a part of each of these components may be realized by any combination of hardware, firmware, software, and the like, without limiting to realization by software with programs. Also, at least a part of each of these components may be realized using a user-programmable integrated circuit, such as a FPGA (Field-Programmable Gate Array) or microcontroller, for example. In this case, this integrated circuit may be used to realize a program formed by each of the above components. Moreover, at least a part of each of the components may be formed by an ASSP (Application Specific Standard Produce), an ASIC (Application Specific Integrated Circuit, or a quantum processor (quantum computer control chip). Thus, each of the components may be implemented by any of various hardware. The above is applicable to other example embodiments described later. Furthermore, each of these components may be realized with a cooperation of a plurality of computers using, for instance, a cloud computing technology. The above is also applicable to other example embodiments described later.

(4) Calculation Example of Fatigue Level

Next, a calculation example of the fatigue level Df of the test subject will be described. In the following, as an example, a calculation example of the test subject fatigue level Df will be described in which the RRI of the test subject is used as the biological data, the muscle mass of the test subject is used for the normalization process, and the index of the heart rate variability is extracted as the feature of the normalized biological data Dn.

In a case where the fatigue estimation model is a linear model, the fatigue estimation device 1 calculates a vector "Y" (including a case of one element) representing the test subject fatigue level Df based on the following formula (1).

$$Y = W^T X \qquad (1)$$

A vector "X" (including a case of one element) represents the index of the heart rate variability, which is the feature of the normalized biological data Dn, and a matrix "W" (also including a case of 1×1) represents a coefficient matrix of a linear model. Here, the matrix W represents a plurality of parameters obtained in advance by learning based on a plurality of sets for the vector Y and the vector X (that is, a learning data set), and is stored in advance in the fatigue estimation model storage unit 42. In this case, a relatively reliable physical fatigue score derived from, for instance, a jump height or a questionnaire result or the like is used as the vector Y in the learning data set.

In the formula (1), when the vector X is rewritten using a normalization function "g" and a feature calculation function "Φ" for calculating the features from the normalized RRI, the following formula (2) is derived.

$$Y = \sum W_j^T \Phi_j(g(RRI_i, \rho_i)) \qquad (2)$$

In the formula (2), a "RRI$_i$" denotes the RRI of the test subject "i" and "pi" denotes the muscle mass of the test subject i. Note that the normalized function g is, for instance, the max-min normalization, the z-score normalization, or the like, and the feature calculation function $\lambda_j$ corresponds to, for instance, a Max function, a Min function, a Median function, or the like, and outputs a vector of one or more elements. A coefficient vector W$_j$ denotes a vector corresponding to a jth column of a coefficient matrix W.

In general, the muscle mass is related to a maximum heart rate; the greater the muscle mass, the less fatiguing it is. Accordingly, according to the formula (2), since the fatigue estimation device 1 normalizes the RRI which is the biological data based on the muscle mass p of the test subject, it is possible to accurately calculate the test subject fatigue level Df without regard to individual differences in test subjects.

Next, specific examples (a first specific example and a second specific example) of the normalization function g in the formula (2) will be described.

The first specific example of the normalization function g is a function which divides RRI which is biological data by the muscle mass p which is the attribute of the test subject. In this case, the normalization function g in the formula (2) is expressed by the following formula (3).

$$g(RRI_i, \rho_i) = RRI_i / \rho_i \qquad (3)$$

By using the normalization function g, it is possible for the fatigue estimation device 1 to reduce the RRI after normalization (that is, the normalized biomedical data Dn) as the muscle mass ρ is greater, and accurately calculate the test subject fatigue level Df.

The second specific example of the normalization function g is a function which normalizes the RRI based on the maximum value "$\rho_{max}$" and the minimum value "$\rho_{min}$" of the muscle mass ρ with the population as a population in a case where there is a population of the test subject having a common attribute. For instance, in the case of a sports team with 20 members as a target population, a maximum muscle mass among the 20 members is defined as the $\rho_{max}$, and a minimum muscle mass is defined as the $\rho_{min}$. In this case, the normalization function g in the formula (2) is expressed by the following formula (4).

$$g(RRI_i, \rho_i) = RRI_i \times \{(\rho_{max} - \rho_i)/(\rho_{max} - \rho_{min})\} \qquad (4)$$

Therefore, in the second specific example, the muscle masses $\rho_{max}$ and $\rho_{min}$ for each population to be inspected are stored in advance in the storage device 4 or the memory 12. Next, in a case of performing the fatigue estimation of the test subject, the fatigue estimation device 1 calculates the test subject fatigue level Df of the test subject based on the formula (4) by using the muscle masses $\rho_{max}$ and $\rho_{min}$ of the population to which the test subject belongs.

Note that even with the second specific example of the normalization function g, the fatigue estimation device 1 can normalize the RRI according to the muscle masse which are the attribute of the test subject, and can accurately calculate the test subject fatigue level Df.

In the second specific example, the maximum muscle mass $\rho_{max}$ and the minimum muscle mass $\rho_{min}$ stored in the storage device 4 or the memory 12 are preferably updated at regular intervals. In this case, an update frequency may be determined depending on the activity status of the population to which the test subject belongs. For instance, in a case of targeting the population of athletes, the update frequency may be different depending on whether they are in season or not, considering that muscle mass fluctuates less in an off-season. Similarly, the muscle mass ρ stored in the attribute information storage unit 41 may suitably be updated depending on the activity status of the test subject at the regular intervals.

Figure 4:
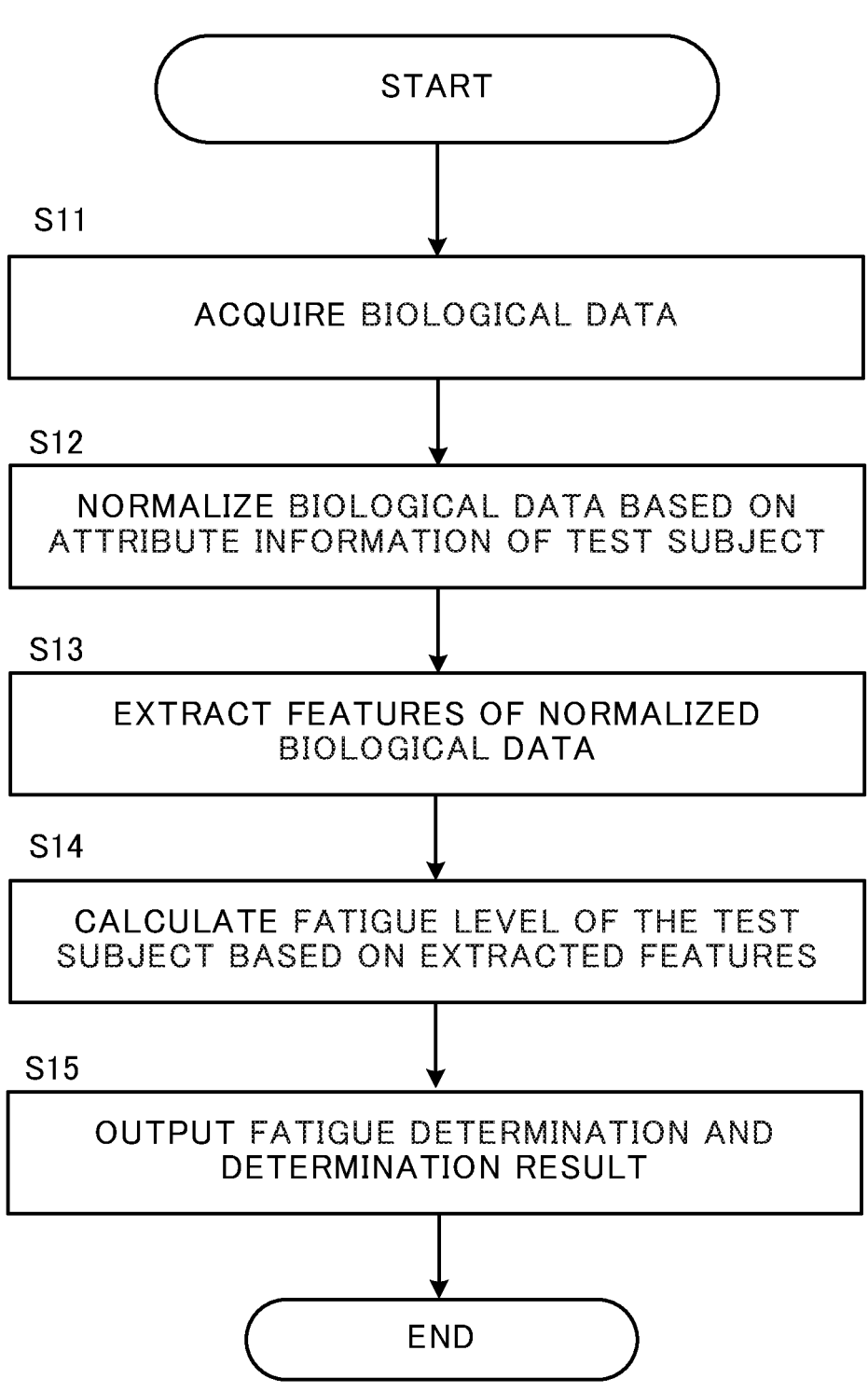
FIG. 4 illustrates an example of a flowchart executed by the fatigue estimation device in the first example embodiment.

FIG. 4 is an example of a flowchart for a process performed by the fatigue estimation device 1 in the first example embodiment. The fatigue estimation device 1 repeatedly executes the process of the flowchart depicted in FIG. 4.

First, the normalization process unit 14 of the fatigue estimation device 1 receives the sensor signal S3 from the sensor 5 via the interface 13, and acquires the biological data to which the normalization process is performed (step S11). Then, the normalization process unit 14 acquires the attribute information of the test subject by referring to the attribute information storage unit 41 of the storage device 4 through the interface 13, and normalizes the biological data acquired in step S11 based on the acquired attribute information of the test subject (step S12). Accordingly, the normalization process unit 14 generates the normalized biological data Dn.

Then, the feature extraction unit 15 performs a process for extracting the features of the normalized biological data Dn (step S13). Next, the fatigue estimation unit 16 calculates the test subject fatigue level Df based on the features extracted by the feature extraction unit 15 in step S13 (step S14). In this case, the fatigue estimation unit 16 forms the fatigue estimation model by referring to the fatigue estimation model storage unit 42, and calculates the test subject fatigue level Df by inputting the features extracted in step S13 into the fatigue estimation model which has been formed.

Next, the fatigue determination unit 17 determines the fatigue condition of the test subject based on the test subject fatigue level Df calculated by the fatigue estimation unit 16 in step S14, and the output control unit 18 outputs a determination result by the fatigue determination unit 17 (step S15). In this case, the output control unit 18, for instance, by displaying the determination result or outputting sound by the fatigue determination unit 17, to notify the fatigue state of the test subject to the test subject or a manager of the test subject.

(6) Modifications

Next, modifications preferable for the first example embodiment will be described. The following modifications may be applied in combination.

First Modification

The fatigue estimation unit 16 may calculate the test subject fatigue level Df using the features of the biological data prior to the normalization in addition to the features of the normalized biological data Dn.

In this case, the fatigue estimation model is a model for outputting the test subject fatigue level Df in response to inputs of the features of the normalized biological data Dn and the features of the biological data, and the parameters of such the fatigue estimation model are stored in advance in the fatigue estimation model storage unit 42. The fatigue estimation unit 16 can suitably calculate the test subject fatigue level Df by using the fatigue estimation model based on the features of the normalized biological data Dn and the features of the biological data prior to the normalization.

Second Modification

The fatigue estimation device 1 may not have the feature extraction unit 15. In this case, the fatigue estimation model stored in the fatigue estimation model storage unit 42 is a model for outputting the test subject fatigue level Df when the normalized biological data Dn are inputted, and the fatigue estimation unit 16 uses this fatigue estimation model to calculate the test subject fatigue level Df from the normalized biological data Dn output by the normalization process unit 14.

Third Modification

In addition to the attribute information of the test subject stored in the attribute information storage unit 41, the normalization process unit 14 may further consider user input information (that is, external input by the user) based on the input signal S1 and perform the normalization of the biological data.

For instance, the normalization process unit 14 sets a coefficient "$\alpha$" to be multiplied by "$\rho_i$" in formula (3), and determines the coefficient $\alpha$ based on the user input information. In another example, the normalization process unit 14 sets a coefficient "$\beta$" which is multiplied by the "$(\rho_{max}-\rho_i)/(\rho_{max}-\rho_{min})$" of the formula (4), and determines the coefficient $\beta$ based on the user input information. Here, the user input information may be information directly specifying the coefficient $\alpha$ or the coefficient $\beta$, or may be information indirectly specifying. In the latter case, for instance, the user input information is information indicating a degree to which the test subject is likely to feel tired, and in this case, the normalization process unit 14 determines the coefficient $\alpha$ or the coefficient $\beta$ by referring to a predetermined formula or a lookup table from the degree indicated by the acquired user input information. The coefficient $\alpha$ and the coefficient $\beta$ are set to 1 which is a default value in a case where there is no user input information.

As described above, the normalization process unit 14 adjusts each coefficient used for the normalization based on the input signal S1, so that it is possible to suitably generate the normalized biological data Dn accurately normalized so as not to depend on the individual difference of the test subject.

Moreover, instead of the input signal S1 or in addition to this input signal S1, the normalization process unit 14 may adjust parameters used for the normalization of the biological data based on environmental information representing an environment at time of measurement of biological data.

In this case, for instance, the environmental information indicates one or more index values which represent the environment such as temperature, humidity, illumination, weather, and the like when the test subject is measured by the sensor 5. The normalization process unit 14 may acquire the environmental information by receiving output signals from a thermometer, a hygrometer, an illuminance sensor, and the like installed at the location, and may receive the environmental information corresponding to an inspection place from a server device which manages weather information and the like at each point. Next, the normalization process unit 14 determines the coefficient used for the normalization (for instance, the above-described coefficient $\alpha$ or coefficient $\beta$) by referring to a predetermined formula, the lookup table or the like based on the acquired environmental information. In this case, the normalization process unit 14 can suitably generate the normalized biological data Dn which are independent of individual differences of the test subjects and the inspection environments.

Second Example Embodiment

Figure 5:
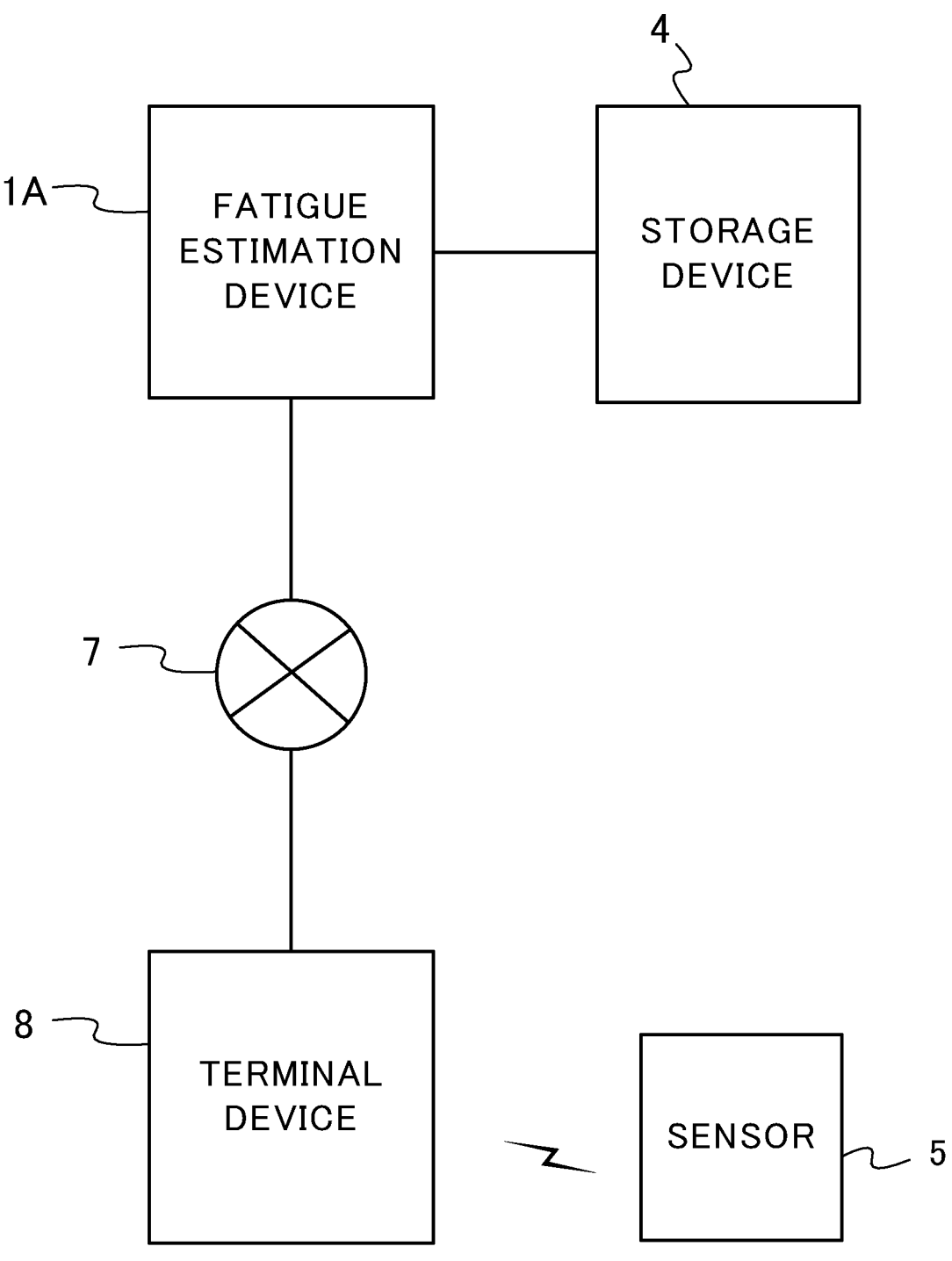
FIG. 5 illustrates a schematical configuration of a fatigue estimation system according to a second example embodiment.

FIG. 5 illustrates a schematic configuration of a fatigue estimation system 100A according to a second example embodiment. The fatigue estimation system 100A according to the second example embodiment is a system of a server client model, and a fatigue estimation device 1A functioning as a server device performs the process of the fatigue estimation device 1 in the first example embodiment. In the following, the same components as in the first embodiment will be indicated with the same numerals as appropriate, and the description thereof will be omitted.

As illustrated in FIG. 5, the fatigue estimation system 100A mainly includes a fatigue estimation device 1A which functions as a server, the storage device 4 which stores data necessary for a fatigue estimation process, and a terminal device 8 which functions as a client. The fatigue estimation device 1A and the terminal device 8 perform data communications via a network 7.

The terminal device 8 is a terminal including an input function, a display function, and a communication function, and functions as the input device 2 and the output device 3 illustrated in FIG. 1. The terminal device 8 may be, for instance, a personal computer, a tablet type terminal, a PDA (Personal Digital Assistant), or the like. The terminal device 8 sends the biological data (that is, information corresponding to the sensor signal S3 in FIG. 1) of the test subject outputted by the sensor 5, information based on user inputs, or the like, to the fatigue estimation device 1A.

The fatigue estimation device 1A includes the same hardware configuration as the hardware configuration of the fatigue estimation device 1 illustrated in FIG. 2, and the processor 11 of the fatigue estimation device 1A includes a functional block illustrated in FIG. 2. Next, the fatigue estimation device 1A receives information acquired by the fatigue estimation device 1 illustrated in FIG. 1 from the input device 2 and the sensor 5, from the terminal device 8 via the network 7. Moreover, in response to a request from the terminal device 8, the fatigue estimation device 1A sends an output signal indicating information concerning the fatigue level of the test subject whom the biological data are detected by the sensor 5, to the terminal device 8 through the network 7. Accordingly, it is possible for the fatigue estimation device 1A to suitably present the information concerning the fatigue level to the user of the terminal device 8.

Third Example Embodiment

Figure 6:
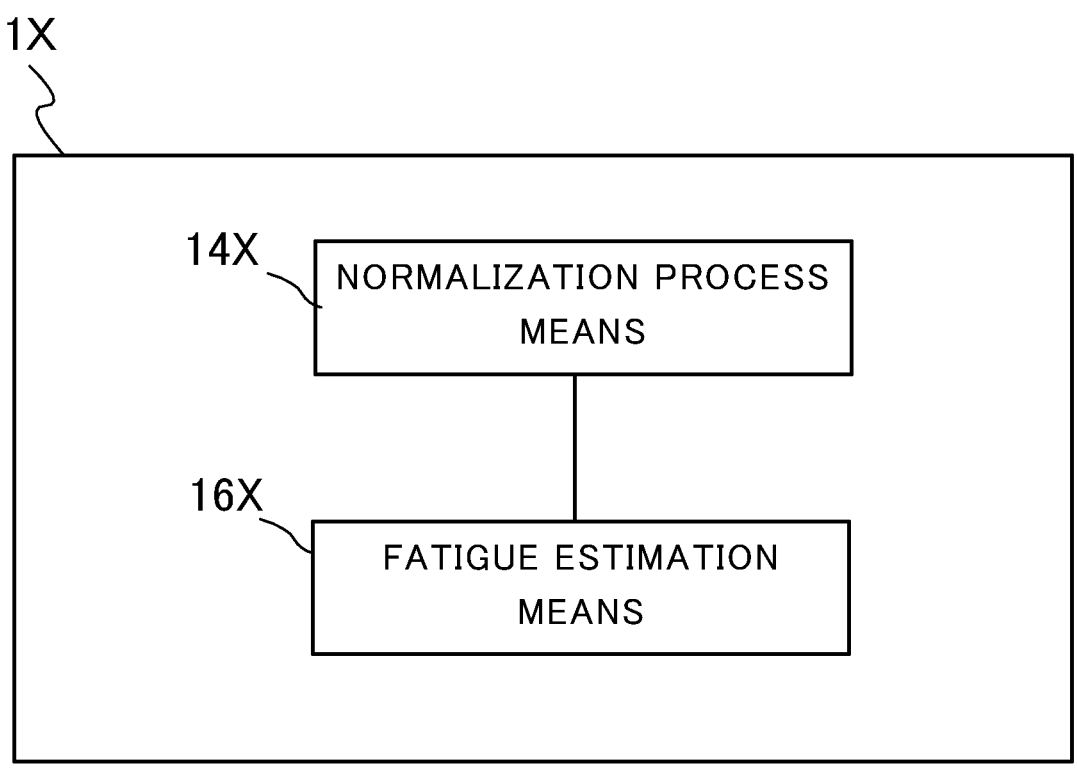
FIG. 6 is a block diagram of a fatigue estimation device in a third example embodiment.

FIG. 6 is a block diagram of a fatigue estimation device 1X according to a third example embodiment. The fatigue estimation device 1X mainly has a normalization process means 14X and a fatigue estimation means 16X. The fatigue estimation device 1X may be formed by a plurality of devices.

The normalization process means 14X performs the normalization process with respect to the biological data of the test subject based on the attribute of the test subject. The normalization process means 14X may be the normalization process unit 14 in the first example embodiment (including modifications, the same applies hereinafter) or the second example embodiment.

The fatigue estimation means 16X estimates the fatigue level of the test subject based on the biological data after the normalization process. The fatigue estimation means 16X may be the fatigue estimation unit 16 in the first example embodiment or the second example embodiment.

Figure 7:
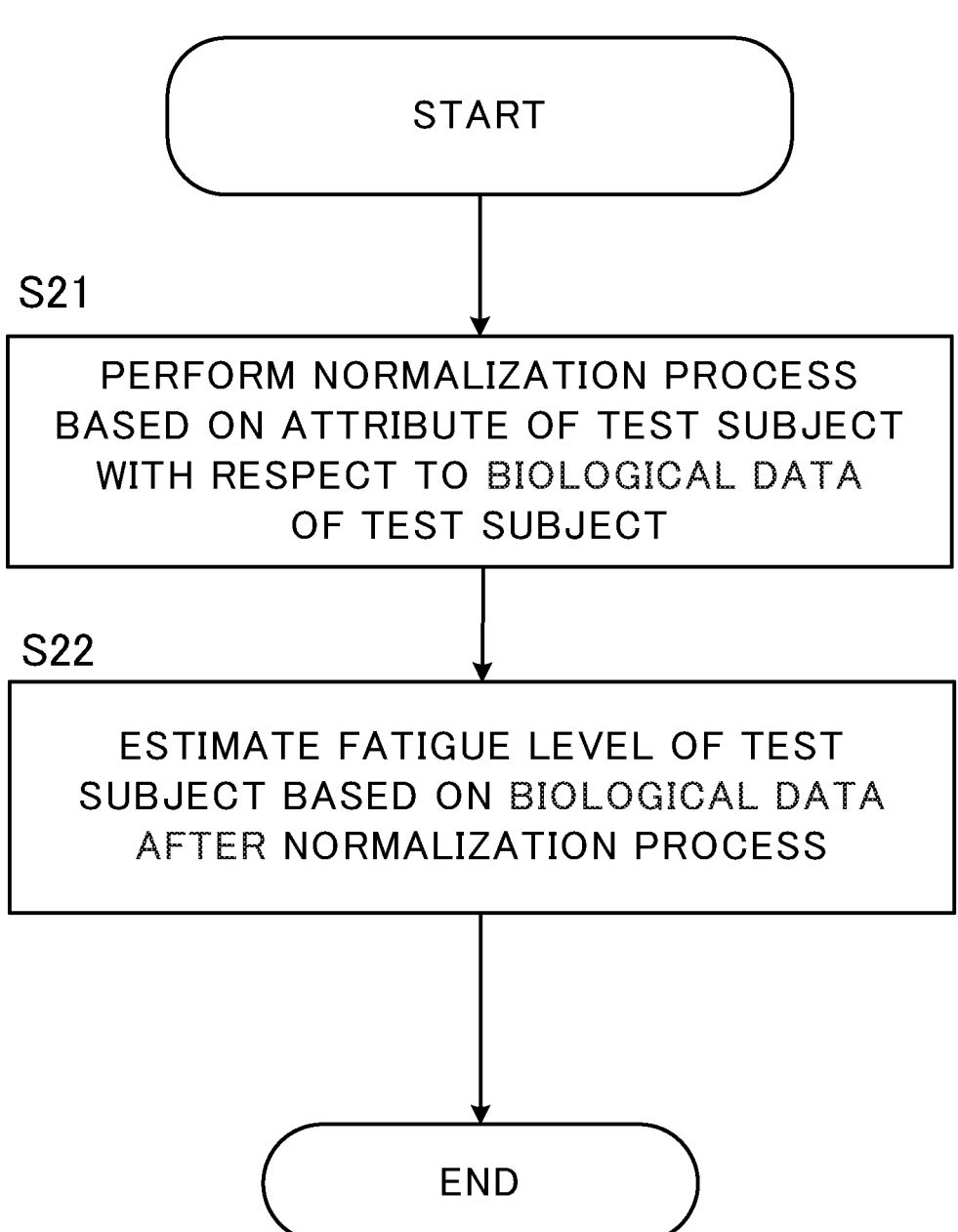
FIG. 7 is an example of a flowchart executed by the fatigue estimation device in the third example embodiment.

FIG. 7 illustrates an example of a flowchart in which the fatigue estimation device 1X performs in the third example embodiment. First, with respect to the biological data of the test subject, the normalization process means 14X performs the normalization process based on the attribute of the test subject (step S21). The fatigue estimation means 16X estimates the fatigue level of the test subject based on the biological data after the normalization process (step S22).

The fatigue estimation device 1X according to the third example embodiment, it is possible to accurately estimate the fatigue level of the test subject.

In the example embodiments described above, the program is stored by any type of a non-transitory computer-readable storage medium (non-transitory computer readable storage medium) and can be supplied to a processor or the like that is a computer. The non-transitory computer-readable storage medium include any type of a tangible storage medium. Examples of the non-transitory computer readable storage medium include a magnetic storage medium (that is, a flexible disk, a magnetic tape, a hard disk drive), a magnetic-optical storage medium (that is, a magnetic optical disk), a CD-ROM (Read Only Memory), a CD-R, a CD-R/W, a solid-state memory (that is, a mask ROM, a PROM (Programmable ROM), an EPROM (Erasable PROM), a flash ROM, a RAM (Random Access Memory)). The program may also be provided to the computer by any type of a transitory computer readable storage medium. Examples of the transitory computer readable storage medium include an electrical signal, an optical signal, and an electromagnetic wave. The transitory computer readable storage medium can provide the program to the computer through a wired channel such as wires and optical fibers or a wireless channel.

In addition, a part or all of the example embodiments described above may also be described as the following supplementary notes, but not limited thereto.

(Supplementary Note 1)

A fatigue estimation device comprising:

a normalization process means configured to perform a normalization process based on an attribute of a test subject with respect to biological data of the test subject; and a fatigue estimation means configured to estimate a fatigue level of the test subject based on the biological data after the normalization process.

(Supplementary Note 2)

The fatigue estimation device according to supplementary note 1, further comprising a feature extraction means configured to extract features of the biological data after the normalization process, wherein the fatigue estimation means estimates the fatigue level based on the features.

(Supplementary Note 3)

The fatigue estimation device according to supplementary note 1 or 2, wherein the attribute corresponds to a muscle mass of the test subject, the normalization process means performs the normalization process based on the muscle mass of the test subject.

(Supplementary Note 4)

The fatigue estimation device according to supplementary note 1 or 2, wherein the attribute is at least any one of an age, a gender, an occupation, or a type of sport which the test subject performs or a position in the sport; and the normalization process means performs the normalization process based on at least any one of the age, the gender, the occupation, or the type of sport which the test subject performs or the position in the sport.

(Supplementary Note 5)

The fatigue estimation device according to any one of supplementary notes 1 to 4, wherein the fatigue estimation means calculates the fatigue level based on a fatigue estimation model which has been trained to output the fatigue level estimated regarding the test subject of the biological data in a case of inputting the biological data or the features of the biological data.

(Supplementary Note 6)

The fatigue estimation device according to any one of supplementary notes 1 to 5, wherein the normalization process means adjusts parameters used for the normalization process based on external inputs.

(Supplementary Note 7)

The fatigue estimation device according to any one of supplementary notes 1 to 6, wherein the normalization process means adjusts parameters used for the normalization process based on environmental information representing an environment at time of a measurement of the biological data.

(Supplementary Note 8)

The fatigue estimation device according to any one of supplementary notes 1 to 7, further comprising a fatigue determination means configured to determine a state concerning a fatigue of the test subject; and an output control means configured to output regarding a result of a determination.

(Supplementary Note 9)

A fatigue estimation method performed by a computer, the fatigue estimation method comprising:

performing a normalization process based on an attribute of a test subject with respect to biological data of the test subject; and estimating a fatigue level of the test subject based on the biological data after the normalization process.

(Supplementary Note 10)

A recording medium storing a program, the program causing a computer to perform a process comprising:

performing a normalization process based on an attribute of a test subject with respect to biological data of the test subject; and estimating a fatigue level of the test subject based on the biological data after the normalization process.

The above description of the present invention is with reference to the embodiments, but the present invention is not limited to the above embodiments. Various changes can be made in the composition and details of the present invention that can be understood by those skilled in the art within the scope of the present invention. In other words, the present invention includes, of course, various transformations and modifications that those skilled in the art would be able to make in accordance with the entire disclosure and technical concept, including the scope of the claims. In addition, the disclosures in the above-mentioned patent documents cited above shall be incorporated herein by reference.

DESCRIPTION OF SYMBOLS

1, 1A, 1X Fatigue estimation device
2 Input device
3 Output device
4 Storage device
5 Sensor
8 Terminal device
100, 100A Fatigue estimation system

What is claimed is:

1. A fatigue estimation device comprising:

at least one memory configured to store instructions; and at least one processor configured to execute the instructions to:

receive, from a sensor device, biological data including an R-R Interval of a test subject which have been measured by the sensor device;

acquiring attribute information including a muscle mass of the test subject;

perform a normalization process that adjusts differences based on respective attributes of test subjects by dividing the R-R Interval by the muscle mass, which is used as the attribute of the test subject, based on the muscle mass included in the attribute information of the test subject with respect to the R-R Interval included in the biological data of the test subject;

extract a heart rate variability which is an index of an autonomic neural tension as features, based on the biological data after the normalization process; and estimate a fatigue level of the test subject based on the features, wherein (a) the at least one memory further stores a trained fatigue estimation model generated using a dataset normalized according to physiological attributes and environmental parameters;

(b) the processor is configured to dynamically adjust the parameters in real time based on both the environmental information and a stored physiological attribute of the test subject;

(c) the normalization process comprises an adaptive normalization that compensates for inter-subject physiological variability and environmental interference in the biological data;

(d) the extracted features comprise time-domain features and frequency-domain features derived from the normalized biological data; and (e) the processor is configured to estimate the fatigue level by inputting the extracted features into the trained fatigue estimation model, wherein the model outputs a fatigue score indicative of at least one of a physical fatigue state or a mental fatigue state of the test subject.

2. The fatigue estimation device according to claim 1, wherein the attribute corresponds to a muscle mass of the test subject, and the processor performs the normalization process based on the muscle mass of the test subject.

3. The fatigue estimation device according to claim 1, wherein the attribute is at least any one of an age, a gender, an occupation, or a type of sport which the test subject performs or position in the sport; and the processor performs the normalization process based on at least any one of the age, the gender, the occupation, or the type of sport which the test subject performs or position in the sport.

4. The fatigue estimation device according to claim 1, wherein the processor calculates the fatigue level based on a fatigue estimation model which has been trained to output the fatigue level estimated regarding the test subject of the biological data in a case of inputting the biological data or the features of the biological data.

5. The fatigue estimation device according to claim 1, wherein the processor adjusts parameters used for the normalization process based on external inputs.

6. The fatigue estimation device according to claim 1, wherein the processor is further configured to determine a state concerning a fatigue of the test subject; and output control means configured to output regarding a result of a determination.

7. A fatigue estimation method performed by a computer, the fatigue estimation method comprising:

receiving, from a sensor device, biological data including an R-R Interval of a test subject which have been measured by the sensor device;

acquiring attribute information including a muscle mass of the test subject;

performing a normalization process that adjusts differences based on respective attributes of test subjects by dividing the R-R Interval by the muscle mass, which is used as the attribute of the test subject, based on the muscle mass included in the attribute information of the test subject with respect the R-R Interval included in the biological data of the test subject;

extracting a heart rate variability which is an index of an autonomic neural tension as features, based on the biological data after the normalization process; and estimating a fatigue level of the test subject based on the features, wherein (a) the at least one memory further stores a trained fatigue estimation model generated using a dataset normalized according to physiological attributes and environmental parameters;

(b) the processor is configured to dynamically adjust the parameters in real time based on both the environmental information and a stored physiological attribute of the test subject;

(c) the normalization process comprises an adaptive normalization that compensates for inter-subject physiological variability and environmental interference in the biological data;

(d) the extracted features comprise time-domain features and frequency-domain features derived from the normalized biological data; and (e) the processor is configured to estimate the fatigue level by inputting the extracted features into the trained fatigue estimation model, wherein the model outputs a fatigue score indicative of at least one of a physical fatigue state or a mental fatigue state of the test subject.

8. A non-transitory computer readable recording medium storing a program, the program causing a computer to perform a process comprising:

receiving, from a sensor device, biological data including an R-R Interval of a test subject which have been measured by the sensor device;

acquiring attribute information including a muscle mass of the test subject;

performing a normalization process that adjusts differences based on respective attributes of test subjects by dividing the R-R Interval by the muscle mass, which is used as the attribute of the test subject, based on the muscle mass included in the attribute information of the test subject with respect to the R-R Interval included in the biological data of the test subject;

extracting a heart rate variability which is an index of an automatic neural tension as features, based on the biological data after the normalization process; and estimating a fatigue level of the test subject based on the features, wherein (a) the at least one memory further stores a trained fatigue estimation model generated using a dataset normalized according to physiological attributes and environmental parameters;

(b) the processor is configured to dynamically adjust the parameters in real time based on both the environmental information and a stored physiological attribute of the test subject;

(c) the normalization process comprises an adaptive normalization that compensates for inter-subject physiological variability and environmental interference in the biological data;

(d) the extracted features comprise time-domain features and frequency-domain features derived from the normalized biological data; and (e) the processor is configured to estimate the fatigue level by inputting the extracted features into the trained fatigue estimation model, wherein the model outputs a fatigue score indicative of at least one of a physical fatigue state or a mental fatigue state of the test subject.

9. The fatigue estimation device according to claim 1, wherein the processor adjusts parameters used for the normalization process based on environmental information representing an environment at time of a measurement of the biological data.

* * * * *